(12) United States Patent
Nakamura et al.

(10) Patent No.: US 12,329,534 B2
(45) Date of Patent: Jun. 17, 2025

(54) BIOLOGICAL EXAMINATION DEVICE AND BIOLOGICAL INFORMATION ANALYSIS METHOD

(71) Applicant: MAXELL, LTD., Kyoto (JP)

(72) Inventors: Yasuaki Nakamura, Tokyo (JP); Akihiko Kandori, Tokyo (JP); Tomohiko Mizuguchi, Tokyo (JP)

(73) Assignee: MAXELL, LTD., Kyoto (JP)

( * ) Notice: Subject to any disclaimer, the term of this patent is extended or adjusted under 35 U.S.C. 154(b) by 177 days.

(21) Appl. No.: 17/923,401

(22) PCT Filed: Apr. 23, 2021

(86) PCT No.: PCT/JP2021/016425
§ 371 (c)(1),
(2) Date: Nov. 4, 2022

(87) PCT Pub. No.: WO2021/225081
PCT Pub. Date: Nov. 11, 2021

(65) Prior Publication Data
US 2023/0131401 A1  Apr. 27, 2023

(30) Foreign Application Priority Data

May 8, 2020  (JP) ................................ 2020-082583

(51) Int. Cl.
*A61B 5/00* (2006.01)
*A61B 5/05* (2021.01)
(Continued)

(52) U.S. Cl.
CPC .............. *A61B 5/4205* (2013.01); *A61B 5/05* (2013.01); *A61B 5/1122* (2013.01);
(Continued)

(58) Field of Classification Search
CPC ....... A61B 5/4205; A61B 5/11; A61B 5/1126; A61B 5/6822
See application file for complete search history.

(56) References Cited

U.S. PATENT DOCUMENTS

2008/0306373 A1* 12/2008 Kandori ................. A61B 7/008
600/407
2009/0227907 A1  9/2009 Kandori et al.
(Continued)

FOREIGN PATENT DOCUMENTS

DE  102018010332 A1  1/2020
JP  2009-213592 A  9/2009
(Continued)

OTHER PUBLICATIONS

Lee, J. C., Seo, H. G., Lee, W. H., Kim, H. C., Han, T. R., & Oh, B.-M. (2016). Computer-assisted detection of swallowing difficulty. Computer Methods and Programs in Biomedicine, 134, 79-88 (Year: 2016).*

(Continued)

*Primary Examiner* — Serkan Akar
*Assistant Examiner* — Aminah Asghar
(74) *Attorney, Agent, or Firm* — Rimon P.C.

(57) ABSTRACT

Provided is a biological examination apparatus and a biological information analysis method capable of quickly grasping a two-dimensional motions of the up-down and front-back directions of the thyroid cartilage and the lingual bone accompanied by a swallowing sound as swallowing dynamics by a non-invasive examination. In the biological examination apparatus of the present invention, an up-down motion component associated with an up-down motion of the thyroid cartilage and a front-back motion component associated with a front-back motion of the thyroid cartilage are extracted from a fitting result obtained by fitting a model function modeling a swallowing motion to distance infor- (Continued)

mation based on detection data detected by a larynx portion displacement detector, and a two-dimensional trajectory data indicating behavior trajectories of an up-down direction and a front-back direction of the thyroid cartilage is generated based on the extracted up-down motion component and the extracted front-back motion component.

12 Claims, 11 Drawing Sheets

(51) Int. Cl.
    *A61B 5/11*     (2006.01)
    *A61B 7/00*     (2006.01)
    *A61B 7/02*     (2006.01)

(52) U.S. Cl.
    CPC .......... *A61B 5/7278* (2013.01); *A61B 5/7425* (2013.01); *A61B 5/743* (2013.01); *A61B 7/008* (2013.01); *A61B 7/023* (2013.01)

(56) References Cited

U.S. PATENT DOCUMENTS

| | | | |
|---|---|---|---|
| 2012/0000300 A1* | 1/2012 | Sunagawa | A61B 5/4023 73/865.4 |
| 2015/0079570 A1 | 3/2015 | Michiwaki et al. | |
| 2020/0022639 A1* | 1/2020 | Shimuta | A61B 5/11 |
| 2020/0037947 A1 | 2/2020 | Shimuta et al. | |
| 2020/0060604 A1 | 2/2020 | Mohammadi et al. | |

FOREIGN PATENT DOCUMENTS

| | | |
|---|---|---|
| JP | 2013-017694 A | 1/2013 |
| JP | 2018-130199 A1 | 8/2018 |
| JP | 2020-511206 A | 4/2020 |
| WO | 2013/146436 A1 | 10/2013 |
| WO | 2018/180779 A1 | 10/2018 |

OTHER PUBLICATIONS

Mao, S., Zhang, Z., Khalifa, Y., Donohue, C., Coyle, J. L., & Sejdic, E. (2019). Neck sensor-supported hyoid bone movement tracking during swallowing. Royal Society Open Science, 6(7), 181982. (Year: 2019).*

International Search Report issued in corresponding International Application No. PCT/JP2021/016425, dated Jun. 29, 2021, w/ English Translation (6 pages).

Office Action issued in the corresponding Chinese Application No. 202180033395.3 dated Dec. 5, 2024, w/ English Translation.

* cited by examiner

BIOLOGICAL EXAMINATION DEVICE AND BIOLOGICAL INFORMATION ANALYSIS METHOD

CROSS REFERENCE TO RELATED APPLICATIONS

This application is the U.S. National Phase under 35 U.S.C. § 371 of International Application No. PCT/JP2021/016425, filed on Apr. 23, 2021, which claims the benefit of Japanese Application No. 2020-082583, filed on May 8, 2020, the entire contents of each are hereby incorporated by reference.

TECHNICAL FIELD

The present invention relates to a biological examination apparatus for performing an examination related to swallowing of a living body, and a biological information analysis method for analyzing biological information obtained with the swallowing of a living body.

BACKGROUND ART

Pneumonia is known as one of major causes of death. Among them, aspiration pneumonia induced by dysphagia, which means a swallowing disorder, accounts for about 60% or more.

The main causative disease of dysphagia is stroke, and it is known that dysphagia occurs in 80% of the patients in acute phase. In addition, it is also known that proportion of dysphagia increases as the age increases even without a clear causative disease such as stroke, and in an aging society, it is expected that aspiration pneumonia and dysphagia will increase in the future.

Therefore, various examinations for diagnosing dysphagia have been conventionally attempted. For example, video fluoroscopic examination of swallowing (VF) is generally known as a method for accurately evaluating and grasping dysphagia. In this VF, motion of a food bolus at the time of swallowing in an examinee and behavior of a lingual bone/larynx portion are monitored using a food bolus containing a contrast medium such as barium sulfate and an X-ray fluoroscopic apparatus. In this case, a swallowing motion is a series of quick motions and is therefore generally recorded in a video and evaluated. However, attention needs to be paid to VF because it is an examination that potentially has a possibility of aspiration, asphyxiation, or the like, and also has problems such as exposure, time restriction, and high cost because an X-ray fluoroscopic apparatus that is a large apparatus is required. Furthermore, videoendoscopic examination of swallowing (VE), which evaluates dysphagia using an endoscope, is also known, but has problems similar to VF. As described above, a clinical examination such as VF or VE can be accurately diagnosed because throat motion is directly observed, but the clinical examination is highly invasive and requires predetermined equipment, and thus cannot be easily performed anywhere.

On the other hand, as a simple examination method for dysphagia, screening examinations such as palpation (repetitive saliva swallowing test (RSST)), auscultation (cervical auscultation method), observation (water drinking examination and food examination), or subjective evaluation including a questionnaire are known, but there is a problem that quantitative evaluation is difficult and reproducibility and objectivity are poor although the screening examinations can be performed as a daily examination.

In view of the above problems, in recent years, some methods for sharing and recording a swallowing state have been proposed. For example, Patent Literature 1 discloses an apparatus in which a microphone is attached to a neck, audio data corresponding to auscultation is saved as digital data, and swallowing is detected by a waveform analysis. Furthermore, Patent Literature 2 discloses a biological examination apparatus in which a magnetic coil is attached to a neck in addition to the microphone, motion data of thyroid cartilage at the time of swallowing corresponding to palpation is saved as digital data in addition to the audio data, and an examination regarding swallowing of a living body and a result thereof are displayed. Specifically, by disposing a transmission coil and a reception coil so as to sandwich the thyroid cartilage, the biological examination apparatus measures, as distance information between the coils, displacement in a horizontal direction of a thyroid cartilage portion caused in association with a two-dimensional behavior of the up-down and front-back directions of the lingual bone at the time of swallowing. According to such an examination form, the distance information and audio information corresponding to palpation and auscultation can be acquired simultaneously and non-invasively, whereby the distance information and the audio information can be combined to evaluate the swallowing motion.

CITATION LIST

Patent Literature

Patent Literature 1: JP 2013-017694 A
Patent Literature 2: JP 2009-213592 A

SUMMARY OF INVENTION

Technical Problem

Meanwhile, in the biological examination apparatus of Patent Literature 2 described above, the distance information and the audio information are independently displayed as time-series waveforms. Therefore, an evaluation of the swallowing state is performed by comparing two types of waveforms, that is, a motion waveform based on the distance information and a swallowing sound waveform based on the audio information with respect to a timing of a temporal change and the like. However, in particular, the motion waveform based on the distance information is a result of indirectly observing the behavior of the lingual bone through the thyroid cartilage, and a two-dimensional motion of the up-down and front-back directions of the thyroid cartilage is indirectly assumed as one-dimensional motion of left and right. Therefore, it is difficult to interpret actual swallowing dynamics from the time-series waveform, and an examiner has to estimate swallowing behavior comprehensively from waveform changes of the audio information and the distance information. In such an evaluation form based on display of two independent time-series waveforms, there is a problem that it is difficult to quickly grasp what the swallowing behavior is specifically.

The present invention has been made in view of the above circumstances, and an object of the present invention is to provide a biological examination apparatus and a biological information analysis method capable of quickly grasping a two-dimensional motion of the up-down and front-back directions of the thyroid cartilage and the lingual bone accompanied with the swallowing sound as the swallowing dynamics by a non-invasive examination.

Solution to Problem

In order to solve the above problems, a biological examination apparatus according to the present invention includes a processor configured to process detection data from a larynx portion displacement detector configured to detect a change in a distance between two positions in a larynx portion of an examinee caused by behavior of a thyroid cartilage in an up-down direction and a front-back direction at the time of swallowing, wherein the processor extracts an up-down motion component associated with an up-down motion of the thyroid cartilage and a front-back motion component associated with a front-back motion of the thyroid cartilage from a fitting result obtained by fitting a model function modeling a swallowing motion to distance information based on the detection data detected by the larynx portion displacement detector, and generates two-dimensional trajectory data indicating behavior trajectories of the up-down direction and the front-back direction of the thyroid cartilage based on the extracted up-down motion component and the extracted front-back motion component.

With respect to distance information based on the detection data, that is, a W-shaped distance waveform 701 (wherein a horizontal axis represents time and a vertical axis represents a distance between two positions) indicating the temporal change in the distance between the two positions in the larynx portion of the examinee caused by the behavior in the up-down direction and the front-back direction of the thyroid cartilage at the time of swallowing, illustrated as an example in FIGS. 11A and 11B, the present inventors have recognized that two-dimensional motions (the front-back motion and the up-down motion) of the thyroid cartilage and the lingual bone are embedded in a one-dimensional (left-right) space due to a pyramidal shape of the thyroid cartilage, and have modified the way of grasping the components in the distance waveform 701 to a unique way different from the conventional one, thereby finding an innovative information presentation form in which the two-dimensional motion of the up-down and front-back directions of the thyroid cartilage and the lingual bone accompanied with the swallowing sound can be quickly grasped as the swallowing dynamics. Specifically, in the distance waveform 701, a downwardly convex waveform component is generated in a series of behavior from rising to falling of the thyroid cartilage, and an upwardly convex waveform component is generated in a series of behavior from advancing to reversing of the thyroid cartilage. However, the present inventors have found a biological information analysis form that a fitting result obtained by fitting a model function modeling the swallowing motion to the distance waveform 701 is obtained by the way of regarding a gently downwardly convex waveform 710 and a sharply upwardly convex waveform 720 as a superposition as illustrated in FIG. 11B, which is different from the conventional way of regarding as a combination of this distance waveform 701 of a W type with a downwardly convex waveform 710a, an upwardly convex waveform 720, and a downwardly convex waveform 710b as illustrated in FIG. 11A, a front-back motion component associated with the front-back motion of the thyroid cartilage corresponding to the upwardly convex waveform 720 and an up-down motion component associated with the up-down motion of the thyroid cartilage corresponding to the downwardly convex waveform 710 are extracted from the fitting result, and then the two-dimensional trajectory data indicating behavior trajectories in the up-down direction and the front-back direction of the thyroid cartilage based on the extracted up-down motion component and the extracted front-back motion component is generated.

According to the above configuration of the present invention, since the fitting result is obtained by fitting the model function modeling the swallowing motion to the distance information based on the detection data detected by the larynx portion displacement detector, the motion of the thyroid cartilage (the lingual bone) can be reproduced two-dimensionally in a non-invasive manner (modeling of the swallowing motion). Since behavior components related to all the motion directions of the thyroid cartilage at the time of swallowing, that is, the two front-back motion component and up-down motion component corresponding to the motions in the up-down direction and the front-back direction, respectively, are extracted from the fitting result, and the two-dimensional trajectory data indicating the behavior trajectories of the thyroid cartilage in the up-down direction and the front-back direction is generated based on these two components, as in Patent Literature 2 described above, it is also possible to quickly grasp the two-dimensional motion in the up-down and front-back directions of the thyroid cartilage (the lingual bone) as swallowing dynamics without requiring comprehensive estimation of the swallowing behavior (to quickly grasp what the swallowing behavior is specifically). In other words, according to the present invention, it is possible to visualize the swallowing dynamics by modeling and decomposing the components of the swallowing motion, and as a result, it is possible to easily evaluate dysphagia without requiring skillfulness.

Furthermore, in the above configuration, the larynx portion displacement detector may adopt any detection form as long as the changes in the distance between the two positions in the larynx portion of the examinee caused by the behavior in the up-down direction and the front-back direction of the thyroid cartilage at the time of swallowing can be detected. For example, the larynx portion displacement detector may include the transmission coil and the reception coil that are arranged so as to sandwich the thyroid cartilage from both sides and transmit and receive the high-frequency signal, or may detect the change in the distance by three-dimensionally photographing the larynx portion (the thyroid cartilage) with the stereo camera or the like and analyzing image data thereof.

Furthermore, in the above configuration, the processor may generate the two-dimensional trajectory data individually indicating the behavior trajectories over time in each of the up-down direction and the front-back direction of the thyroid cartilage based on the up-down motion component and the front-back motion component. According to this, it is also possible to individually grasp the trajectories of the up-down motion and the front-back motion of the thyroid cartilage, and this can also contribute to detailed analysis of the swallowing motion.

Furthermore, in the above configuration, the processor may generate the two-dimensional trajectory data simultaneously showing the behavior in the up-down direction and the front-back direction of the thyroid cartilage by one trajectory graph based on the up-down motion component and the front-back motion component. According to this, the swallowing dynamics including the two pieces of physical information (up-down motion information and front-back motion information of the thyroid cartilage) can be integrated into one trajectory graph and visualized, and the two-dimensional motions of the up-down and front-back directions of the thyroid cartilage (the lingual bone) can be quickly grasped. In this case, it is preferable that the two-dimensional trajectory data is generated as coordinate data indicated on a coordinate plane defined by two coordinate axes orthogonal to each other, one of the coordinate axes corresponds to a trajectory data value of the front-back motion component, and the other coordinate axis corresponds to a trajectory data value of the up-down motion component. In fact, it has been confirmed by the present inventors that a display form based on such trajectory data values substantially corresponds to the motion trajectories of the lingual bone in the swallowing dynamics analysis such as the lingual bone motion by a swallowing contrast examination (VF).

Furthermore, in the above configuration, the biological examination apparatus may further include a swallowing sound detector that detects a swallowing sound when the examinee swallows, and the processor may generate a swallowing sound waveform indicating the temporal change in an amplitude of the swallowing sound based on the detection data detected by the swallowing sound detector, and generate identification display data for identifying and displaying a plot of each trajectory data value on the trajectory graph according to a magnitude of the amplitude of the swallowing sound by temporally associating the swallowing sound waveform and the trajectory graph.

According to this, the behavior of the larynx portion and the change in the swallowing sound can be integrated into one trajectory graph and visualized based on the two pieces of physical information (the distance information and the audio information) obtained from the larynx portion displacement detector and the swallowing sound detector, so that the swallowing dynamics such as the timing of the swallowing motion and the swallowing sound can be non-invasively quickly recognized. In addition, since the plot of each trajectory data value on the trajectory graph is identified and displayed according to the magnitude of the amplitude of the swallowing sound, it is possible to visually and quickly recognize at which timing the swallowing sound is emitted and to quickly determine at which timing a substance put in a mouth is fed from esophagus to stomach.

Furthermore, in the above configuration, the "identify and display" may be in any display form as long as the trajectory data values having different amplitudes of the swallowing sound can be identified by color-coding the plots of the trajectory data values according to the magnitude of the amplitude of the swallowing sound, changing the magnitude or shape of the plots (the marks) of the trajectory data values according to the magnitude of the amplitude of the swallowing sound, or the like.

Furthermore, in the above configuration, the processor may generate supplementary display data for displaying supplementary information including a predetermined feature point associated with the fitting result, a predetermined feature point associated with the swallowing sound waveform, and occurrence time of the trajectory data values plotted on the trajectory graph to be superimposed on the trajectory graph. According to this, the trajectory graph display can be complemented by the supplementary information related to the behavior of the larynx portion and the change in the swallowing sound, and amount of information that can be read from the trajectory graph can be increased. Therefore, the evaluation of dysphagia can be performed more accurately and quickly. In addition, examples of the "feature point" include a singular point, an inflection point, and the like, in the waveform including the fitting result (for example, a fitted motion waveform) and an upper limit peak value and a lower limit peak value of the swallowing sound waveform or the waveform related thereto.

Furthermore, in the above configuration, the processor may generate reference display data for displaying, the reference information including a transition direction of the trajectory graph and the predetermined feature amounts calculated from the trajectory graph, together with the trajectory graph. According to this, information that is difficult to grasp only from the trajectory graph can be added and displayed together with the trajectory graph, a degree of understanding of the trajectory graph can be enhanced, and this can contribute to an accurate and quick evaluation of dysphagia. In addition, examples of the "feature amounts" include a maximum amount of displacement in the front-back direction of the thyroid cartilage, a maximum amount of displacement in the up-down direction, a time difference between times when the motion waveform and the swallowing sound waveform take maximum values, a ratio of the time difference to variance values of displacement in the front-back direction of the thyroid cartilage, and the like.

Furthermore, the present invention also provides a biological information analysis method having the characteristics mentioned above. According to such biological information analysis method, it is possible to obtain the same effects as those of the biological examination apparatus mentioned above.

Advantageous Effects of Invention

According to the present invention, from the fitting result obtained by fitting the model function modeling the swallowing motion to the distance information based on the detection data detected by the larynx portion displacement detector, the up-down motion component associated with the up-down motion of the thyroid cartilage and the front-back motion component associated with the front-back motion of the thyroid cartilage are extracted, and the two-dimensional trajectory data indicating the behavior trajectories in the up-down direction and the front-back direction of the thyroid cartilage is generated based on the extracted up-down motion component and the extracted front-back motion component. Therefore, the two-dimensional motions of the up-down and front-back directions of the thyroid cartilage and the lingual bone accompanied with the swallowing sound can be quickly grasped as the swallowing dynamics by the non-invasive examination.

DESCRIPTION OF EMBODIMENTS

Hereinafter, one embodiment of the present invention will be described with reference to the drawings.

Figure 1:
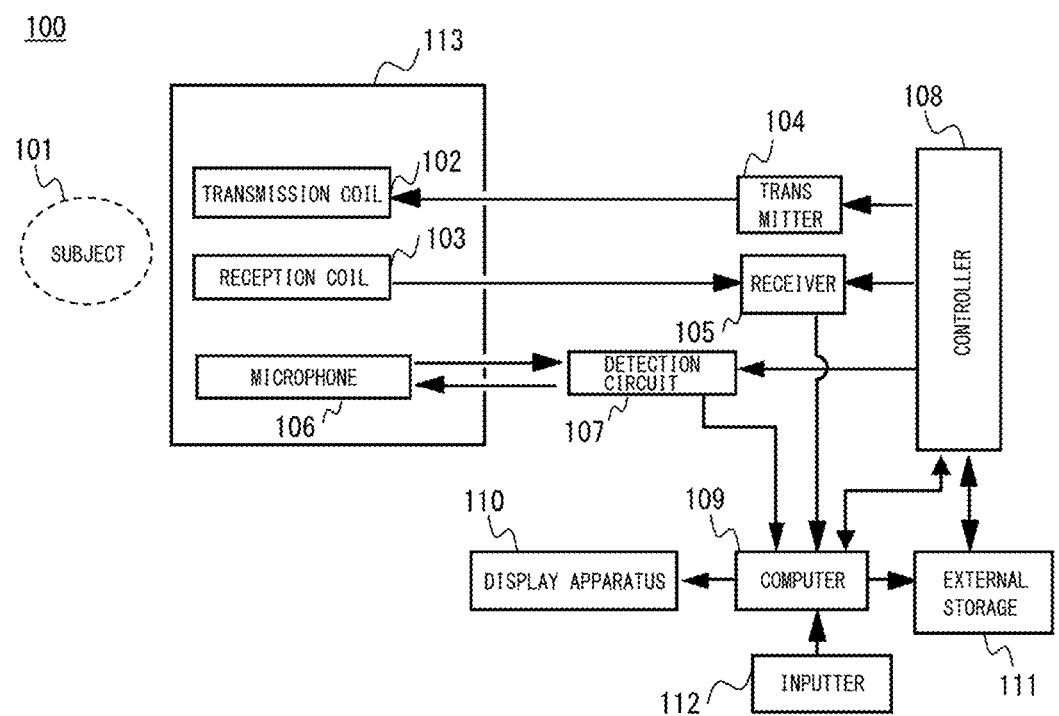
FIG. 1 is a functional block diagram of a biological examination apparatus according to one embodiment of the present invention.

FIG. 1 is a functional block diagram illustrating a configuration example of a biological examination apparatus 100 according to one embodiment of the present invention. As illustrated in FIG. 1, the biological examination apparatus 100 includes a transmission coil 102 and a reception coil 103 as larynx portion displacement detectors that detect a change in a distance between two positions in a larynx portion (a living body part around a thyroid cartilage) of a subject (examinee) 101 caused by behavior in an up-down direction and a front-back direction of the thyroid cartilage (common name: Adam's apple) at the time of swallowing of the subject 101, and a microphone 106 as a swallowing sound detector that detects a swallowing sound when the subject 101 swallows, and these coils 102 and 103 and the microphone 106 are held by a flexible holder 113 described later with reference to FIG. 2.

The transmission coil 102 and the reception coil 103 are arranged to face each other so as to sandwich the thyroid cartilage from both sides, the transmission coil 102 is connected to a transmitter 104, and the reception coil 103 is connected to a receiver 105. Furthermore, the microphone 106 is arranged in a vicinity of the thyroid cartilage of the subject 101, is electrically connected to a detection circuit 107 that detects the swallowing sound captured by the microphone 106 at the time of swallowing, and receives power supply or the like from the detection circuit 107 for operation. In addition, the microphone 106 is preferably a microphone using, for example, a piezoelectric element so as not to pick up ambient sounds other than the swallowing sound as much as possible, but may be a condenser microphone or the like.

Furthermore, the biological examination apparatus 100 further includes a controller 108, a computer 109, a display apparatus 110, an external storage 111, and an inputter 112. The controller 108 controls operations of the transmitter 104, the receiver 105, the detection circuit 107, the computer 109, and the external storage 111, and controls power supply, signal transmission/reception timing, and the like. Moreover, the computer 109 is an information processor including a CPU, a memory, an internal storage, and the like, and performs various arithmetic processing. A control and a calculation performed by the computer 109 are realized by a CPU executing a predetermined program. However, a part of the calculation can also be realized by hardware such as an application specific integrated circuit (ASIC) or a field programmable gate array (FPGA). In addition, the display apparatus 110, the external storage 111, and the inputter 112 are electrically connected to the computer 109.

Furthermore, the display apparatus 110 is an interface that displays a measured waveform and analysis information through the computer 109 on a display. Note that a specific function may be notified by an LED, an audio, or the like. Moreover, the external storage 111 holds data used for various arithmetic processing executed by the computer 109, data obtained by the arithmetic processing, and conditions, parameters, and the like input via the inputter 112, together with the internal storage. In addition, the inputter 112 is an interface for an operator to input conditions and the like necessary for a measurement and the arithmetic processing performed in the present embodiment.

In such configuration, the high-frequency signal generated by the transmitter 104 is transmitted to the transmission coil 102, so that the transmission coil 102 emits a high-frequency magnetic field, and accordingly, a signal received by the reception coil 103 is received by the receiver 105. In addition, the signal received by the receiver 105 is transmitted to the computer 109 as an output voltage measurement value of a voltage between the coils. On the other hand, the swallowing sound captured by the microphone 106 is detected by the detection circuit 107, converted into a voltage signal, and input from the detection circuit 107 to the computer 109 as the output voltage measurement value.

Figure 2:
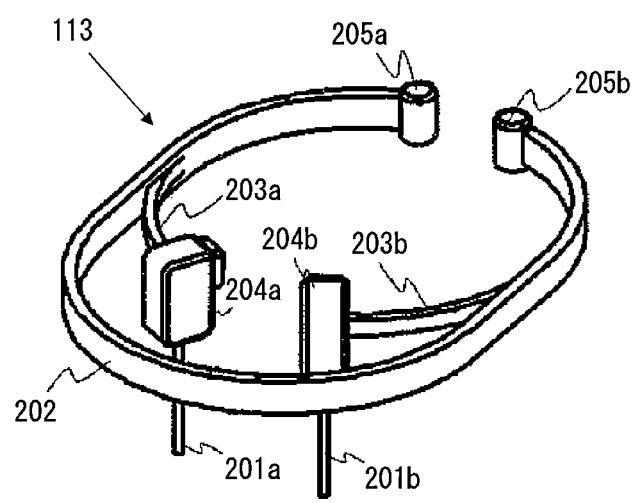
FIG. 2 is a schematic perspective view of a flexible holder that holds a larynx portion displacement detector of the biological examination apparatus of FIG. 1.

In FIG. 2, the flexible holder 113 that holds the transmission/reception coils 102 and 103 and the microphone 106 is shown. The flexible holder 113 is formed of any flexible material such as various resins. As illustrated in FIG. 2, the flexible holder includes a substantially annular neck attachment member 202 to be attached to the neck of the subject 101 using an open end thereof, and a pair of arc-shaped sensor holding member 203a and 203b positioned along substantially the same arc inside the neck attachment member 202. The neck attachment member 202 is integrally coupled so as to hold one end of each of the pair of sensor holding members 203a and 203b on both sides inside thereof, and the other ends of the sensor holding members 203a and 203b are opened to be positioned near the larynx portion of the subject 101. Then, sensors 204a and 204b are arranged at the other ends of the pair of sensor holding members 203a and 203b, respectively, and these sensors 204a and 204b are brought into contact with the larynx portion of the subject 101, and can follow the motion of swallowing (motion of the thyroid cartilage or the like) independently of the neck attachment member 202 together with the sensor holding members 203a and 203b positioned without contacting the neck of the subject 101.

The transmission coil 102 is arranged in one of the sensors 204a and 204b in a fixed state, the reception coil 103 is arranged in the other one in a fixed state, and the microphone 106 is arranged in any one of the sensors 204a and 204b in a fixed state. In particular, in the present embodiment, the transmission coil 102 and the reception coil 103 are attached to the sensors 204a and 204b so as to be arranged in directions easily facing each other (close to a vertical direction of a neck surface of the subject 101), thereby enabling detection with a high signal-to-noise (SN) ratio. Therefore, the microphone 106 and the transmission coil 102 or the reception coil 103 can be arranged at positions substantially orthogonal to each other, and a mixing of a magnetic field noise generated from the microphone 106 into the transmission and/or reception coils 102 and 103 can be reduced. However, corresponding positions of the transmission coil 102 and the reception coil 103 and a position orthogonal to the microphone are not limited to the described arrangement, and may be any position as long as the detection with a sufficiently high SN ratio can be realized.

Furthermore, pressers 205a and 205b to be applied to the neck of the subject 101 are formed in a shape suitable for pressing, such as a cylindrical shape or a spherical shape, at opposing end portions forming the open end of the neck attachment member 202 (portions of the neck attachment member 202 positioned on a back side of the neck of the subject 101). The flexible holder 113 can be easily attached to the neck regardless of the size of the neck of the subject 101 by four pressing points including the two pressers 205a and 205b and the two sensors 204a and 204b provided at the other ends of the sensor holding members 203a and 203b. In addition, the transmission/reception coils 102 and 103 and electric wirings 201a and 201b extending from the microphone 106 built in the sensors 204a and 204b are electrically connected to the transmitter 104, the receiver 105, and the detection circuit 107 illustrated in FIG. 1, respectively.

Figure 3:
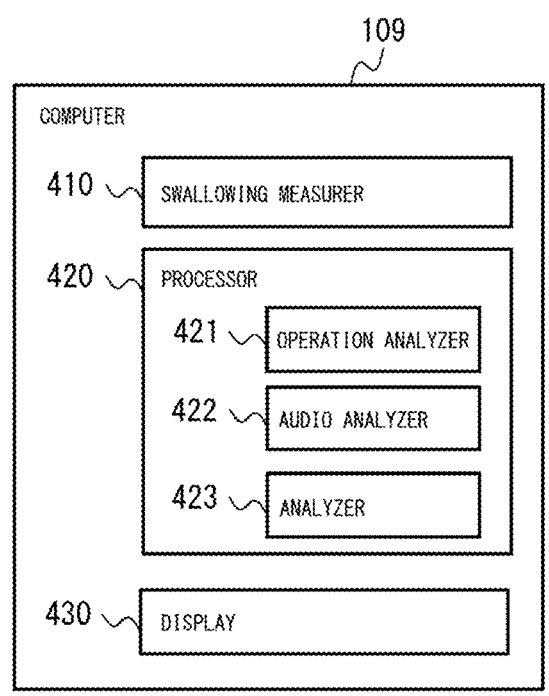
FIG. 3 is a functional block diagram of a computer of the biological examination apparatus of FIG. 1.

FIG. 3 illustrates a functional block diagram of the computer 109. As illustrated in FIG. 3, the computer 109 includes a swallowing measurer 410, a processor 420, and a display 430. The swallowing measurer 410 measures the swallowing motion and the swallowing sound using the transmission coil 102, the reception coil 103, the transmitter 104, the receiver 105, the microphone 106, the detection circuit 107, and the controller 108 described in connection with FIG. 1 (a larynx portion displacement detection step and a swallowing sound detection step). Furthermore, the processor 420 includes an operation analyzer 421 that analyzes the distance information, an audio analyzer 422 that analyzes the swallowing sound that is audio information, and an analyzer 423 that performs analysis by combining the distance information and the swallowing sound, and processes data measured by the swallowing measurer 410 (a processing step). Specifically, as will be described later, the processor 420 obtains the fitting result (in the present embodiment, a fitted waveform 1103 illustrated in FIG. 8A to be described later) obtained by fitting a model function (in the present embodiment, Formula (1) to be described later) modeling the swallowing motion to the distance information (in the present embodiment, data indicating a temporal change in the distance between the coils 102 and 103 arranged so as to sandwich the thyroid cartilage of the subject 101 (the distance waveform 701 illustrated in FIG. 7 to be described later)) based on the detection data detected by the transmission/reception coils 102 and 103, extracts a front-back motion component associated with the front-back motion of the thyroid cartilage (in the present embodiment, a front-back motion component waveform 1105 illustrated in FIG. 8B to be described later or a data value forming the waveform) and an up-down motion component associated with the up-down motion of the thyroid cartilage (in the present embodiment, an up-down motion component waveform 1106 illustrated in FIG. 8B to be described later or a data value forming the waveform) from the fitting result, and generates the two-dimensional trajectory data indicating behavior trajectories of the up-down direction and the front-back direction of the thyroid cartilage based on the extracted up-down motion component and the extracted front-back motion component (in the present embodiment, data for forming a trajectory graph 901 illustrated in FIG. 10 to be described later). Furthermore, as will be described later, the processor 420 generates the swallowing sound waveform indicating a temporal change in the amplitude of the swallowing sound (in the present embodiment, a swallowing sound waveform 801 illustrated in FIG. 9 to be described later) based on the detection data detected by the microphone 106, and generates the identification display data for identifying and displaying the plot of each trajectory data value on the trajectory graph according to the magnitude of the amplitude of the swallowing sound by temporally associating the swallowing sound waveform and the trajectory graph. Moreover, the display 430 displays information (data) measured and processed by the swallowing measurer 410 and the processor 420 on the display apparatus 110 (a display step). In addition, the swallowing measurer 410, the processor 420, and the display 430 operate independently.

Figure 4:
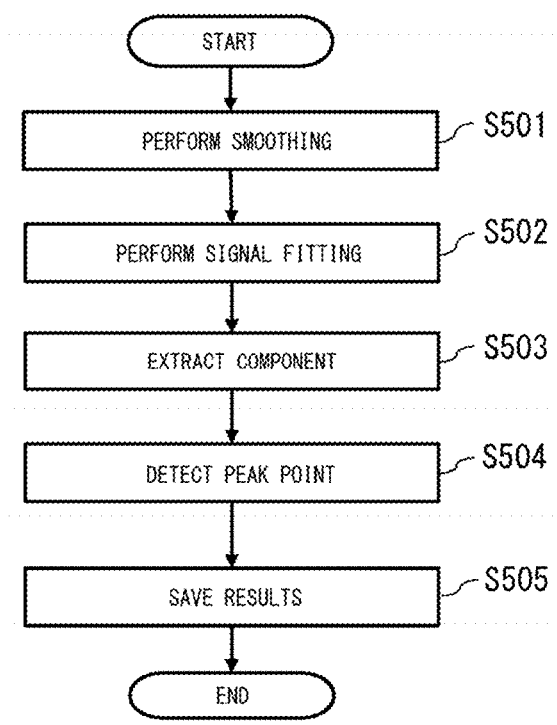
FIG. 4 is a flowchart illustrating a flow of processing of an operation analyzer of a processor of the computer in FIG. 3.

FIG. 4 illustrates the flow of processing of the operation analyzer 421 in the processor 420 of the computer 109 in FIG. 3. The operation analyzer 421 processes the detection data detected by the transmission/reception coils 102 and 103. Specifically, first, in step S501, the operation analyzer 421 performs smoothing on the data measured by the swallowing measurer 410. In particular, in the present embodiment, the smoothing is performed using a piecewise polynomial approximation by the Savitzky-Golay filter. The smoothing in this case is performed by setting the number of windows and the degree of the polynomial to, for example, 5 and 51, respectively. In addition, a smoothing method may be, for example, a simple moving average or the like, and the present invention is not limited by these methods.

Figure 7:
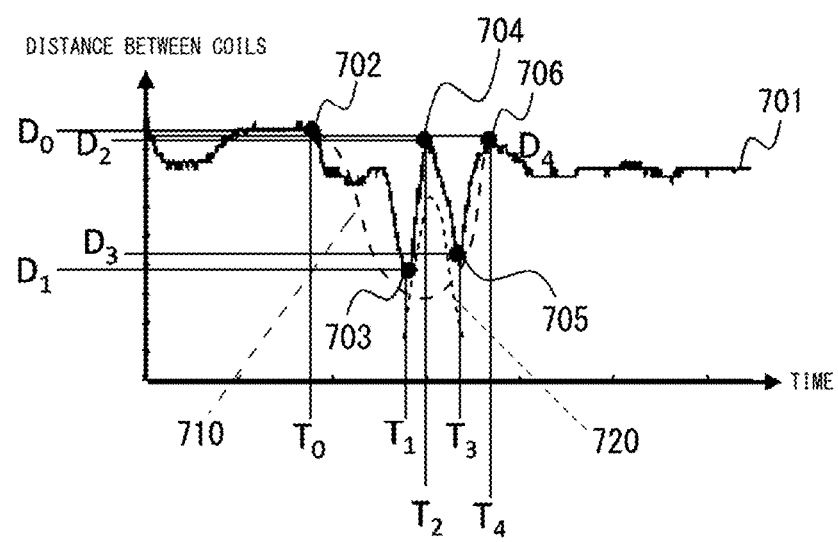
FIG. 7 is a distance waveform diagram based on typical distance information detected by the larynx portion displacement detector of the biological examination apparatus of FIG. 1.

Subsequently, in step S502, fitting is performed on the measurement signal smoothed in step S501. In this regard, FIG. 7 illustrates a typical example of the distance waveform 701 illustrating a temporal change in the distance between the transmission/reception coils 102 and 103, which is a distance between two positions in the larynx portion of the subject 101. Such distance waveform 701 to be measured is a result of observing the two-dimensional motion (the front-back motion and the up-down motion) of the thyroid cartilage (the lingual bone) one-dimensionally (left-and-right), and exhibits a W-shaped waveform shape as illustrated in FIG. 7 since the thyroid cartilage has a pyramidal shape. Specifically, the thyroid cartilage rises as the food bolus is fed into the esophagus from a starting point (time $T_0$) 702 at which the subject 101 starts to swallow the food bolus by putting the food bolus into the mouth, so that the distance between the transmission/reception coils 102 and 103 narrows from $D_0$ to $D_1$, and the distance waveform 701 indicates a first valley portion (a first lower limit peak value; a time $T_1$) 703. Furthermore, in a feeding process of the food bolus, an epiglottis of the subject 101 moves downward, and a path from a nasal cavity to an airway is blocked. Thereafter, when the food bolus passes through the esophagus, the thyroid cartilage moves forward (in a direction in which the face of the subject faces) to open the esophagus, so that the distance between the transmission/reception coils 102 and 103 expands from $D_1$ to $D_2$, and the distance waveform 701 transitions from a first valley portion 703 to a mountain portion (the upper limit peak value; a time $T_2$) 704. Then, when the food bolus completely passes through the esophagus (the epiglottis) and is fed into the stomach, the thyroid cartilage also moves backward as the epiglottis moves upward, so that the distance between the transmission/ reception coils 102 and 103 narrows from $D_2$ to $D_3$, and the distance waveform 701 transitions from a mountain portion 704 to a second valley portion (a second lower limit peak value; a time $T_3$) 705. Thereafter, the thyroid cartilage descends so that the epiglottis and the thyroid cartilage return to their original positions, thereby widening the distance between the transmission/reception coils 102 and 103 from $D_3$ to $D_4$, and the distance waveform 701 transitions from a second valley portion 705 to an ending point (a time $T_4$) 706.

As can be seen from the above, in such a distance waveform 701, a downwardly convex waveform component is generated in a series of behaviors from rising to falling of the thyroid cartilage, and an upwardly convex waveform component is generated in a series of behaviors from advancing to reversing of the thyroid cartilage. Therefore, in the present embodiment, the W-shaped distance waveform 701 is regarded as superposition of a gently downwardly convex waveform 710 (corresponding to the up-down motion component waveform 1106 illustrated in FIG. 8B) and the sharply upwardly convex waveform 720 (corresponding to the front-back motion component waveform 1105 illustrated in FIG. 8B) as distinguished by a short broken line and a long broken line in FIG. 7, and is modeled as the following Formula (1).

$$y(t)=rAP(t)+rHF(t)+d(t)+e \quad \text{[Mathematical Formula 1]}$$

Here, t represents time, y(t) represents a measured distance waveform, rAP(t) represents a component in the front-back direction, rHF(t) represents a component in the up-down direction, d(t) represents a trend component generated from a body motion or the like (for example, an offset from an initial value caused by an individual difference such as a thickness of a neck), and e represents a measurement noise.

Furthermore, in the present embodiment, components rAP and rHF in the front-back direction and the up-down direction are modeled by a normal distribution, and a trend component d(t) is modeled by a linear equation. However, these models may be autoregressive models or nonlinear models, and the present invention is not limited thereto. Moreover, in such modeling of the present embodiment, each component is obtained by a parameter fitting using a mathematical optimization method. In addition, in the present embodiment, the parameter fitting is performed using a nonlinear least squares method, but the present invention is not limited thereto. Furthermore, when the parameter fitting is performed, for example, a constraint that the variance values of rAP is smaller than the variance values of rHF may be provided.

Figure 8A:
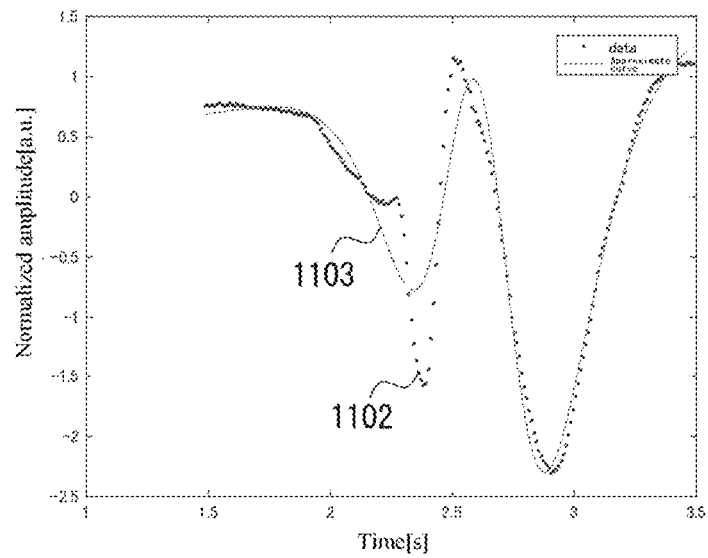
FIG. 8A is distance information based on the detection data detected by the larynx portion displacement detector of the biological examination apparatus of FIG. 1 and a fitted motion waveform (a fitting waveform) obtained from the distance information.

FIG. 8A illustrates the fitting result of the model function (Formula (1)) using such normal distribution. In FIG. 8A, a waveform 1102 formed by a data value represented by a dot corresponds to the distance waveform 701 illustrated in FIG. 7, and the waveform 1103 represented by a solid line is a motion waveform (the fitting waveform) obtained by fitting a model function to the distance information forming the waveform 1102. Here, the horizontal axis is time, and the vertical axis is a normalized amplitude based on the distance between the coils illustrated in FIG. 7.

After the signal fitting step S502 as described above is completed, parameters are extracted from a fitted model function in step S503. In the present embodiment, since the behavior in the front-back direction and the up-down direction of the thyroid cartilage is modeled with independent normal distributions, "amplitude", "average value", and "variance" of each of these behaviors are extracted in step S503. In addition, the "amplitude" corresponds to the magnitude of the motion of the thyroid cartilage, the "average value" corresponds to the time when the motion occurred, and the "variance" corresponds to a duration of the motion.

Figure 8B:
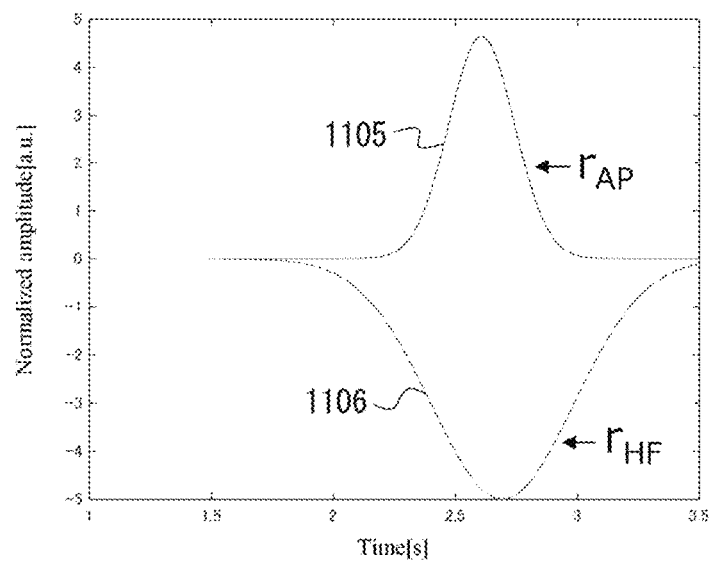
FIG. 8B is a component waveform individually showing behavior trajectories over time in each of an up-down direction and a front-back direction of the thyroid cartilage.

In this regard, FIG. 8B illustrates waveforms (the upwardly convex front-back motion component waveform 1105 and the downwardly convex up-down motion component waveform 1106) obtained by individually extracting and displaying only components in the front-back direction and the up-down direction of the thyroid cartilage from the motion waveform (the fitting waveform) 1103 illustrated in FIG. 8A. As described above, the processor 420 including the operation analyzer 421 of the biological examination apparatus 100 of the present embodiment can generate the two-dimensional trajectory data individually indicating the behavior trajectories over time in each of the up-down direction and the front-back direction of the thyroid cartilage based on the up-down motion component and the front-back motion component.

After the component extraction step S503 ends, in step S504, feature points of the W-shaped waveform, that is, the feature points corresponding to the peak points 702 to 706 (data values of $D_0$ to $D_4$ and $T_0$ to $T_4$) on the distance waveform 701 in FIG. 7 are extracted from the waveform reconstructed using the parameters extracted in step S503. Specifically, in the present embodiment, since the measurement signal is modeled and the components are separated as in Formula (1), the feature points are easily extracted without considering the noise and the trend component. More specifically, as an example, $T_2$ is acquired as an average value of rAP, $T_1$ and $T_3$ are acquired as times indicating the minimum values before and after $T_2$, respectively, and $T_0$ and $T_4$ are acquired as times at points advanced from the average value of rHF by the variance values in negative and positive directions, respectively. Then, $D_0$ to $D_4$ are acquired as values corresponding to the times $T_0$ to $T_4$, respectively.

After the peak value detection step S504 ends, in step S505, the waveforms, the parameters, the feature points, and the like calculated in steps S501 to S504 described above are saved in the internal storage and/or the external storage 111 of the computer 109. Furthermore, the above steps S501 to S505 may be performed during the measurement of the swallowing motion and the swallowing sound by the swallowing measurer 410, or may be performed for a plurality of times.

Figure 5:
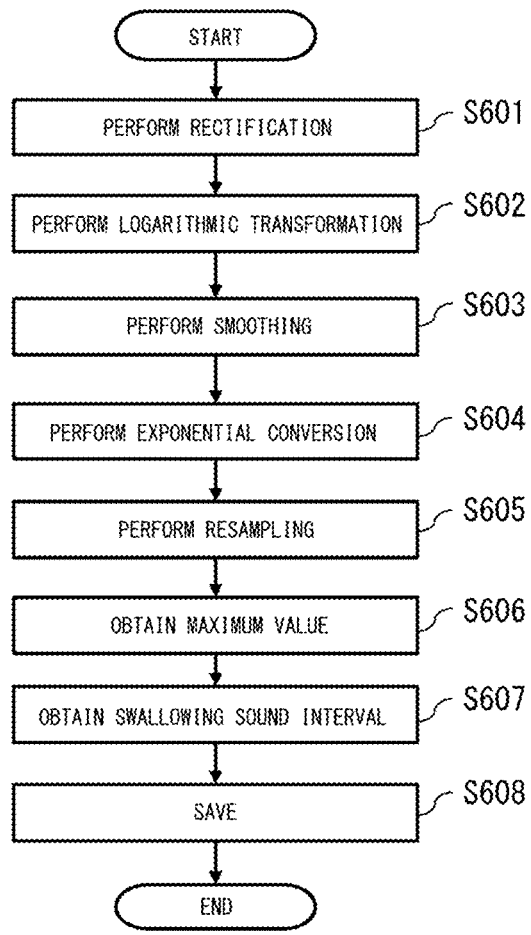
FIG. 5 is a flowchart illustrating a flow of processing of an audio analyzer of the processor of the computer in FIG. 3.
Figure 9:
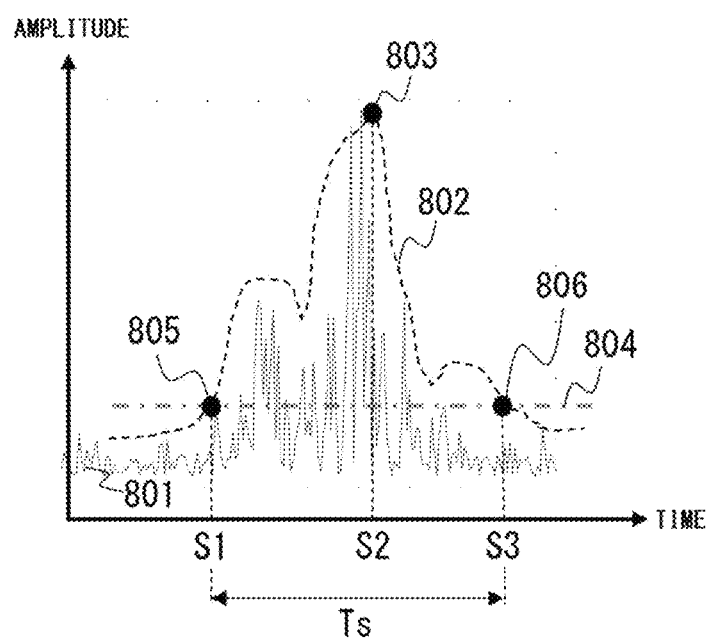
FIG. 9 is a swallowing sound waveform diagram including an envelope based on typical audio information detected by a swallowing sound detector of the biological examination apparatus of FIG. 1.

FIG. 5 illustrates the flow of processing of the audio analyzer 422 of the processor 420 of the computer 109 in FIG. 3. As illustrated in FIG. 5, in step S601, a rectification process is performed on the audio information (generally, an audio signal including both positive and negative values) measured from the microphone 106 through the swallowing measurer 410. Here, the rectification process refers to a process of using an absolute value and converting a negative value into a positive value. FIG. 9 illustrates the swallowing sound waveform 801 obtained by rectifying typical audio information.

In step S602, the signal subjected to the rectification process obtained in step S601 is subjected to logarithmic transformation. This processing can reduce an influence of a spike-like signal mixed in the swallowing sound.

In step S603, the smoothing is performed on the logarithmically transformed signal obtained in step S602. In particular, in the present embodiment, the smoothing process is performed using the moving average, and a window width of the moving average is set to 400 points. Note that the present invention is not limited by this smoothing method.

In step S604, an exponential conversion is performed on the smoothing signal obtained in step S603. Accordingly, a waveform indicating the envelope of the initially measured audio information can be obtained. In FIG. 9, an envelope 802 obtained from such typical audio information (the swallowing sound waveform 801) is indicated by a broken line.

In step S605, an envelope signal obtained in step S604 is resampled. Specifically, in the present embodiment, since sampling frequencies of the audio information and the distance information in the swallowing measurer 410 illustrated in FIG. 3 are 4000 Hz and 100 Hz, respectively, processing of resampling the envelope signal to 1/40 to match the sampling frequency of the distance information is performed.

In step S606, a maximum value as a feature point is obtained for a resampled envelope signal obtained in step S605. This is because an interval in which a maximum amplitude is obtained in the swallowing sound signal (the swallowing sound waveform 801) is considered to indicate a flow of an ingested matter, and is an important feature of the swallowing sound. Therefore, in this step 606, a time S2 corresponding to a peak point 803 indicating the maximum amplitude with respect to the envelope 802 shown in FIG. 9 is obtained.

In step S607, a swallowing sound interval of the resampled envelope signal obtained in step S605 is obtained. In other words, in the envelope 802, the times at both ends of the swallowing sound interval are acquired to obtain a time interval Ts in which the swallowing sound occurs. Specifically, an amplitude threshold 804 indicated by an alternate long and short dash line in FIG. 9 is set, and times $S_1$ and $S_3$ respectively corresponding to points crossing the threshold 804 downward as viewed from the maximum value (the peak point 803) obtained in step S606, that is, a temporally early starting point 805 and a temporally late ending point 806 are acquired as the feature points. Furthermore, in the present embodiment, a value obtained by adding a normalized median absolute deviation to a median is used as the threshold 804. Note that the present invention is not limited by the method of setting the threshold 804, and a value obtained by adding a standard deviation to an average value or the like may be used.

Finally, in step S608, the waveforms, the feature amounts, and the like calculated in steps S601 to S607 described above are saved in the internal storage and/or the external storage 111 of the computer 109. In addition, the above steps S601 to S608 may be performed during the measurement of the swallowing motion and the swallowing sound by the swallowing measurer 410, or may be performed for a plurality of times.

Figure 6:
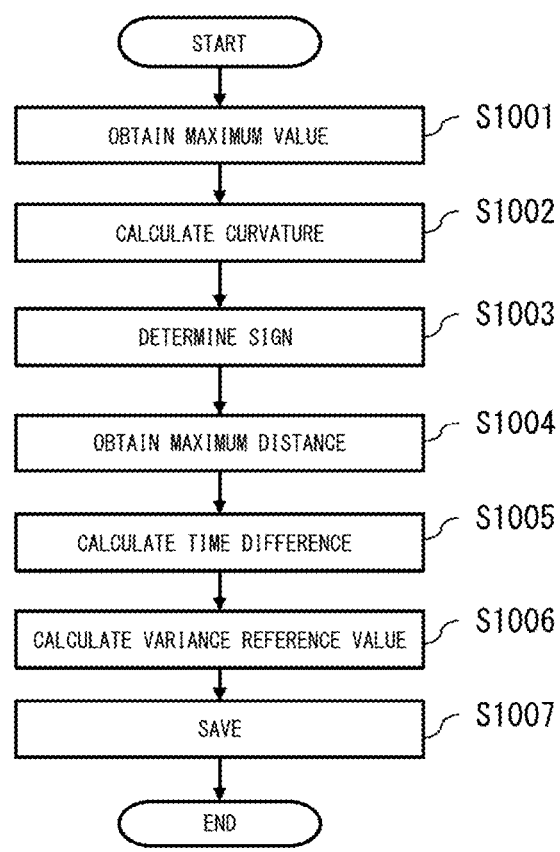
FIG. 6 is a flowchart illustrating a flow of processing of an analyzer of the processor of the computer in FIG. 3.

FIG. 6 illustrates the flow of processing of the analyzer 423 of the processor 420 of the computer 109 in FIG. 3. As illustrated in FIG. 6, in step S1001, a maximum displacement (a maximum value) in the front-back direction and the up-down direction of the motion waveform 1103 (or the distance waveform 701) that is the fitted waveform is calculated.

Figure 10:
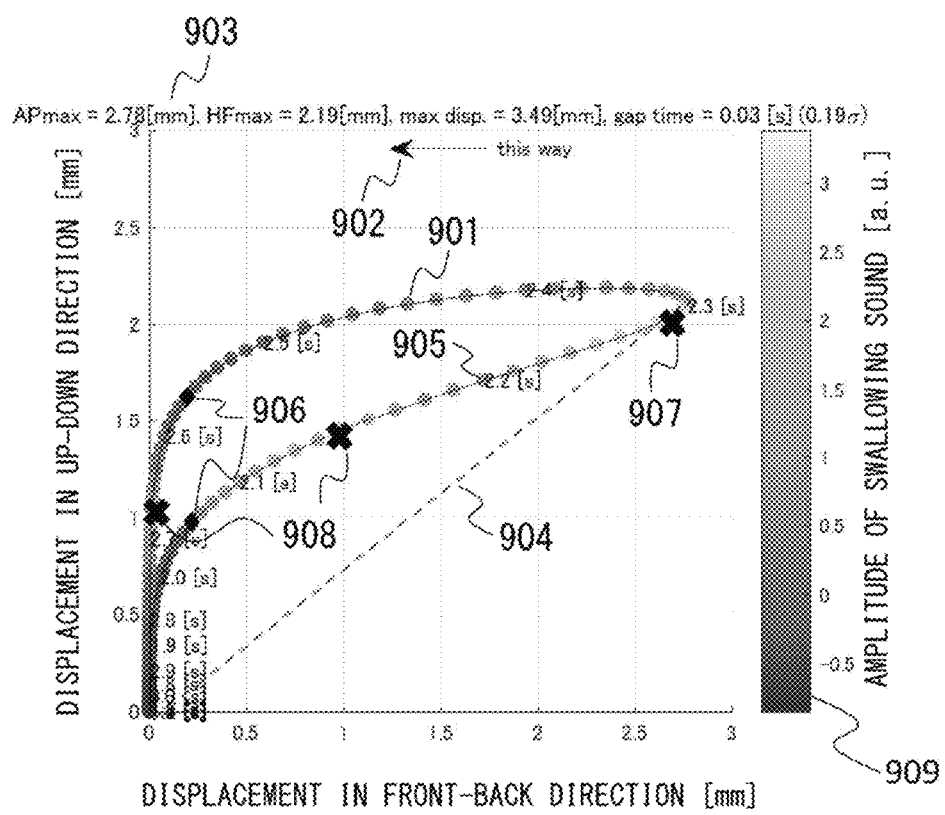
FIG. 10 illustrates an example of a trajectory graph displayed based on two-dimensional trajectory data obtained by the processor of the biological examination apparatus of FIG. 1.
Figure 11A:
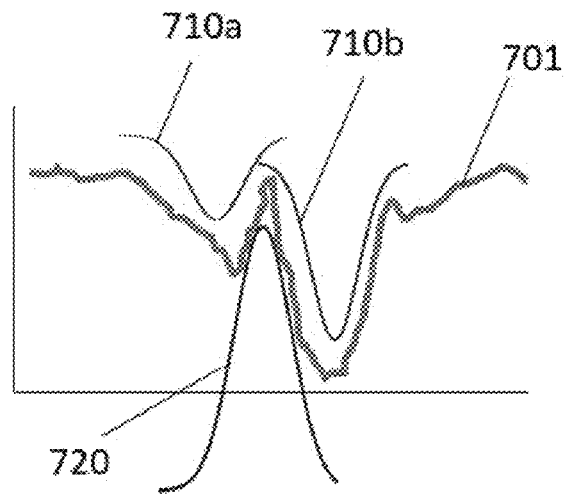
FIG. 11A is a waveform diagram illustrating a conventional way of grasping a component in the distance waveform.
Figure 11B:
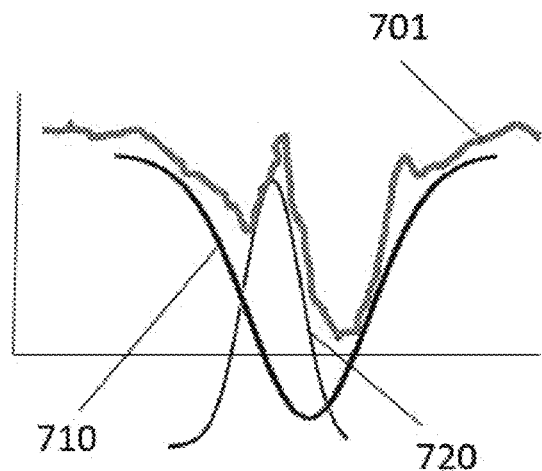
FIG. 11B is a waveform diagram illustrating a way in the present invention of grasping a component in the distance waveform.

In step S1002, a signed curvature of each point on the trajectory graph 901 described in detail below with reference to FIG. 10 is calculated. In step S1002, a time progress direction (the transition direction) of the trajectory graph 901 is extracted, and the signed curvature at each point on the trajectory graph 901 is calculated in order to extract the point having the maximum displacement.

In step S1003, a sign is acquired in the signed curvature obtained in step S1002. Specifically, in the trajectory graph 901, since an amplitude of the curvature is maximized at the point farthest from the coordinate origin, the sign of the point having the maximum curvature is acquired after the curvature of each point on the trajectory graph 901 is calculated. By determining the sign such that a counterclockwise direction is positive and a clockwise direction is negative as a coordinate system, the time progress direction is uniquely obtained. In addition, a factor that determines whether the sign is positive or negative is a magnitude of an average value of the component rAP in the front-back direction and the component rHF in the up-down direction. In the trajectory graph 901 of FIG. 10 to be described later in which the time progress direction is the counterclockwise direction, it is indicated that the average value (that is, the time for taking the maximum value) of the displacement in the front-back direction is earlier than that in the up-down direction.

In step S1004, a geometric distance from the coordinate origin of the point at which the maximum value of the signed curvature calculated in step S1002 is obtained is acquired. In the trajectory graph 901, since the amplitude of the curvature is maximized at the point farthest from the coordinate origin, the geometric distance from the point at which the amplitude of the curvature is maximized to the coordinate origin is calculated. Accordingly, it is possible to acquire a time point (time) at which the displacement is the largest when the components in the up-down direction and the front-back direction of the thyroid cartilage are synthesized.

In step S1005, the time difference between the time for taking the maximum value of the audio information and the time for taking the maximum value of the distance information in the front-back direction is obtained. This is particularly because the time difference using the maximum value is an important parameter in characterizing the swallowing state. In the present embodiment, as can be seen from the display form of the trajectory graph 901 to be described later, this parameter can be not only visually grasped but also displayed as a quantitative value. In addition, the present invention is not limited by these quantitative values, and for example, the area of the region surrounded by the trajectory graph may be displayed as the feature amounts.

In step S1006, a ratio (a ratio of the time difference to the variance values) of the time difference obtained in step S1005 based on the variance values of the model (the front-back motion component waveform 1105 illustrated in FIG. 8B) indicating the component in the front-back direction of the distance information is acquired. Since the swallowing sound is generated at the timing when the thyroid cartilage advances in a healthy subject model, in step S1006, the ratio is calculated in order to display the degree of the deviation in the occurrence of the swallowing sound in an individual.

Finally, in step S1007, the waveforms, the feature amounts, and the like calculated in steps S1001 to the S1006 described above are saved in the internal storage and/or the external storage 111 of the computer 109. In addition, the above steps S1001 to S1007 may be performed during the measurement of the swallowing motion and the swallowing sound by the swallowing measurer 410, or may be performed for a plurality of times.

Based on the processing steps as described above, the processor 420 further generates the two-dimensional trajectory data simultaneously showing the behavior in the up-down direction and the front-back direction of the thyroid cartilage as one trajectory graph 901 (see FIG. 10) based on the up-down motion component and the front-back motion component described above. Specifically, such two-dimensional trajectory data is generated as the coordinate data indicated on the coordinate plane defined by two coordinate axes orthogonal to each other. One of the coordinate axes corresponds to a trajectory data value of a front-back motion component, and the other coordinate axis corresponds to a trajectory data value of an up-down motion component. More specifically, as illustrated in FIG. 10, based on the signal fitting (step S502 in FIG. 4) and the component extraction (step S503 in FIG. 4) by the operation analyzer 421 described above, the data value on the up-down motion component waveform 1106 and the data value on the front-back motion component waveform 1105 described above are temporally associated with each other, and the horizontal axis is plotted as the trajectory data value of the front-back motion component (the displacement in the front-back direction; the normalized amplitude in the front-back motion component waveform 1105), and the vertical axis is plotted as the trajectory data value of an up-down motion component (the displacement in the up-down direction; the normalized amplitude in the up-down motion component waveform 1106). In other words, the horizontal axis indicates the value of the normal distribution having the parameter extracted for rAP of Formula (1) in step S503 of FIG. 4, and the vertical axis indicates the value of the normal distribution having the parameter extracted for rHF of Formula (1).

Such trajectory graph 901 illustrated in FIG. 10 is displayed on the display apparatus 110 via the display 430 of the computer 109. In particular, in the present embodiment, plots of respective trajectory data values on the trajectory graph 901 are identified and displayed according to the magnitude of the amplitude of the swallowing sound, for example, color-coded. In order to realize such identification and display, the processor 420 generates the swallowing sound waveform 801 and the envelope 802 indicating the temporal change of the amplitude of the swallowing sound based on the detection data detected through the microphone 106 as described above, and generates the identification display data for identifying and displaying the plot of each trajectory data value on the trajectory graph 901 according to the magnitude of the amplitude of the swallowing sound by temporally associating the swallowing sound waveform 801 or the envelope 802 with the trajectory graph 901. Furthermore, in the present embodiment in which color-coded display is performed in association with such identification and display, a band graph 909 for reference indicating how the color changes with the magnitude of a swallowing sound amplitude value along the vertical axis is displayed adjacent to the trajectory graph 901. For example, here, an identification and display form is formed such that the larger the amplitude of the swallowing sound, the more yellowish it is, and the smaller the amplitude, the more bluish it is. Alternatively, the identification and display form may be such that color coding is performed in black and white, and the color becomes lighter as the amplitude increases. In addition, the identification and display form is not limited to this, and any display form may be used as long as the trajectory data values having different amplitudes of the swallowing sound can be identified by changing the magnitude or shape of the plot (the mark) of each trajectory data value according to the magnitude of the amplitude of the swallowing sound.

Such trajectory graph 901 in which the trajectory data values are plotted as a time-series scatter diagram displays behaviors of the front-back direction and the up-down direction of the thyroid cartilage separately on two coordinate axes such that the behavior of the thyroid cartilage when swallowing can be quickly grasped. In addition, by displaying the characteristics of the swallowing sound information in addition to the behavior of the swallowing motion in one trajectory graph 901 in this manner, it is possible to visually confirm at which time point the swallowing sound has occurred with respect to the behavior of the thyroid cartilage, and not only to quantitatively grasp the swallowing motion but also to quickly grasp the deviation of the swallowing sound from a normal state and a power of the swallowing sound.

Furthermore, various auxiliary information is added and displayed on the trajectory graph 901. For this purpose, in the present embodiment, the processor 420 generates the supplementary display data for displaying the supplementary information including the predetermined feature point associated with the motion waveform 1103 (or the distance waveform 701), the predetermined feature point associated with the swallowing sound waveform 801 (or the envelope 802), and an occurrence time of the trajectory data values plotted on the trajectory graph 901 to be superimposed on the trajectory graph 901, and also generates the reference display data for displaying the reference information including the transition direction of the trajectory graph 901 and the predetermined feature amounts calculated from the trajectory graph 901 together with the trajectory graph 901.

Specifically, with respect to such an auxiliary display, a reference numeral 902 in FIG. 10 denotes an arrow indicating in which direction the trajectory has progressed (the transition direction of the trajectory graph 901). In the present embodiment, the trajectory starts from the coordinate origin, rotates counterclockwise, and then returns to the coordinate origin. Furthermore, a reference numeral 903 indicates a feature amount calculated from the trajectory graph 901. Specifically, the maximum amount of displacement in the front-back direction, the maximum amount of displacement in the up-down direction, the maximum displacement from the coordinate origin indicated by a reference numeral 904, a time difference ($\sigma$) of the time during which the motion information and the audio information each take the maximum value, and the ratio of the time difference based on the variance values of the displacement (rAP) in the front-back direction are indicated as the feature amounts. These pieces of information are obtained based on the processing by the analyzer 423 described above. In addition, as a method of displaying the feature amounts, the feature amounts may be displayed in a coordinate region of the trajectory graph 901 or may be displayed in another diagram instead of being displayed above the coordinate region of the trajectory graph 901 as in the present embodiment, and the present invention is not limited thereto.

And in FIG. 10, a reference numeral 905 denotes an occurrence time of a trajectory data value plotted on the trajectory graph 901, and is displayed every 0.1 seconds in the present embodiment. Moreover, a reference numeral 906 denotes a peak point in the distance information obtained in step S504 in FIG. 4. In addition, a reference numeral 907 indicates the time point at which the maximum value of the audio information obtained in step S606 of FIG. 5 is obtained. With this display, a time lag between the time point indicating the maximum value of the audio information and the time point indicating the maximum value of the component in the front-back direction of the thyroid cartilage in the distance information can be confirmed in FIG. 5. Furthermore, a reference numeral 908 indicates the starting point 805 and the ending point 806 (see FIG. 9) of the audio information obtained in step S607 of FIG. 5.

As described above, according to the present embodiment, since the fitting result is obtained by fitting the model function modeling the swallowing motion to the distance information based on the detection data detected by the transmission/reception coils 102 and 103, the motion of the thyroid cartilage (the lingual bone) can be reproduced two-dimensionally (modeling of the swallowing motion) in a non-invasive manner, the behavior components related to all the motion directions of the thyroid cartilage at the time of swallowing, that is, the front-back motion component and the up-down motion component respectively corresponding to the motions in the up-down direction and the front-back direction are extracted from the fitting result. Since the two-dimensional trajectory data indicating the behavior trajectories in the up-down direction and the front-back direction of the thyroid cartilage is generated based on these two components, it is also possible to quickly grasp a two-dimensional motions of the up-down and front-back directions of the thyroid cartilage (the lingual bone) as the swallowing dynamics without requiring comprehensive estimation of the swallowing behavior.

Furthermore, the present invention is not limited to the embodiments mentioned above, and various modifications can be made without departing from the gist thereof. For example, in the embodiment mentioned above, the present invention is applied to the behavior of the thyroid cartilage, but the present invention can also be applied to the examination of the motion of a living body part other than the thyroid cartilage. In other words, the present invention can also be applied to analysis of motion of a site other than the larynx portion as long as the site is a body part that makes a motion (a front-back and up-down motion) similar to that of the thyroid cartilage (the lingual bone). Specifically, the present invention can be applied to any body part as long as a change in distance detected by a predetermined detector can be analyzed through decomposing the change in distance into motions in a plurality of directions. In addition, the biological examination apparatus of the present invention may not include the larynx portion displacement detector, the swallowing sound detector, and the display apparatus as described above. In other words, the biological examination apparatus, the larynx portion displacement detector, the swallowing sound detector, and the display apparatus may be configured as separate systems. In addition, a part or all of the embodiments mentioned above may be combined, or a part of the configuration may be omitted from one of the embodiments mentioned above without departing from the gist of the present invention.

The invention claimed is:

1. A biological examination apparatus comprising:
a larynx portion displacement detector including a first electrode and a second electrode arranged to sandwich a thyroid cartilage of an examinee from opposite sides, wherein the larynx portion displacement detector is configured to transmit and receive a signal and detect changes in a distance between the first electrode and the second electrode based on the received signal, and wherein the changes in the distance correspond to physical movement of the thyroid cartilage in an up-down direction and a front-back direction during swallowing;
a swallowing sound detector configured to detect a swallowing sound of the examinee during the swallowing; and
a processor configured to:
receive detection data from the larynx portion displacement detector and convert the detection data into distance information representing the physical movement of the thyroid cartilage;
apply a model function to the distance information to separate the physical movement of the thyroid cartilage into an up-down motion component and a front-back motion component, wherein the motion function is configured to extract directional movement features specific to swallowing behavior;
generate two-dimensional trajectory data based on the up-down motion component and the front-back motion component, wherein the two-dimensional trajectory data graphically represents a movement trajectory of the thyroid cartilage during swallowing in both the up-down direction and the front-back direction directions, and wherein the two-dimensional trajectory data simultaneously shows the movement of the thyroid cartilage in the up-down direction and the front-back direction of the thyroid cartilage by one trajectory graph based on the up-down motion component and the front-back motion component;
generate a swallowing sound waveform indicating a temporal change in an amplitude of the swallowing sound based on detection data from the swallowing sound detector; and
generate identification display data for associating the swallowing sound waveform with the two-dimensional trajectory data, wherein the processor is configured to identify and display each trajectory data value, which is a data point included in the two-dimensional trajectory data, on the one trajectory graph in a manner corresponding to the amplitude of the swallowing sound.

2. The biological examination apparatus according to claim 1, wherein the processor generates the two-dimensional trajectory data by separately generating a time-series behavior trajectory of the thyroid cartilage in the up-down direction and a time-series behavior trajectory of the thyroid cartilage in the front-back direction, based on the up-down motion component and the front-back motion component.

3. The biological examination apparatus according to claim 1, wherein the two-dimensional trajectory data is generated as coordinate data indicated on a coordinate plane defined by two coordinate axes orthogonal to each other, one of the coordinate axes corresponds to a trajectory data value of the front-back motion component, and the other coordinate axis corresponds to a trajectory data value of the up-down motion component.

4. The biological examination apparatus according to claim 1, wherein the processor is further configured to generate supplementary display data for displaying supplementary information including at least one of a predetermined feature point associated with a result of applying the model function to the distance information, a predetermined feature point associated with the swallowing sound waveform, and occurrence time of the each trajectory data value plotted on the one trajectory graph in a superimposed manner on the one trajectory graph.

5. The biological examination apparatus according to claim 1, wherein the processor is further configured to generate reference display data for displaying, together with the one trajectory graph, reference information including at least one of a transition direction of the one trajectory graph and predetermined feature amounts calculated from the one trajectory graph.

6. The biological examination apparatus according to claim 1, wherein the first electrode is one of a transmission coil and a reception coil and the second electrode is another of the transmission coil and the reception coil, the transmission coil and the reception coil transmitting and receiving a high-frequency signal.

7. A biological information analysis method, comprising:
arranging a first electrode and a second electrode to sandwich a thyroid cartilage of an examinee from opposite sides, transmitting and receiving a signal, and detecting changes in a distance between the first electrode and the second electrode based on the received signal, wherein the changes in the distance correspond to physical movement of the thyroid cartilage in an up-down direction and a front-back direction during swallowing; and
receiving detection data related to the changes in the distance and convert the detection data into distance information representing the physical movement of the thyroid cartilage;
applying a model function to the distance information to separate the physical movement of the thyroid cartilage into an up-down motion component and a front-back motion component, wherein the motion function is configured to extract directional movement features specific to swallowing behavior; generating two-dimensional trajectory data based on the up-down motion component and the front-back motion component, wherein the two-dimensional trajectory data graphically represents a movement trajectory of the thyroid cartilage during swallowing in both the up-down direction and the front-back direction directions, and wherein the two-dimensional trajectory data simultaneously shows the movement of the thyroid cartilage in the up-down direction and the front-back direction of the thyroid cartilage by one trajectory graph based on the up-down motion component and the front-back motion component;
detecting a swallowing sound of the examinee during the swallowing;
generating a swallowing sound waveform indicating a temporal change in an amplitude of the swallowing sound based on detection data of the swallowing sound;
generating identification display data for associating the swallowing sound waveform with the two-dimensional trajectory data; and
identifying and displaying each trajectory data value, which is a data point included in the two-dimensional trajectory data, on the one trajectory graph in a manner corresponding to the amplitude of the swallowing sound.

8. The biological information analysis method according to claim 7, wherein generating the two-dimensional trajectory data includes separately generating a time-series behavior trajectory of the thyroid cartilage in the up-down direction and a time-series behavior trajectory of the thyroid cartilage in the front-back direction, based on the up-down motion component and the front-back motion component.

9. The biological information analysis method according to claim 7, wherein the two-dimensional trajectory data is generated as coordinate data indicated on a coordinate plane defined by two coordinate axes orthogonal to each other, one of the coordinate axes corresponds to a trajectory data value of the front-back motion component, and the other coordinate axis corresponds to a trajectory data value of the up-down motion component.

10. The biological information analysis method according to claim 7, further comprising generating supplementary display data for displaying supplementary information including at least one of a predetermined feature point associated with a result of applying the model function to the distance information, a predetermined feature point associated with the swallowing sound waveform, and occurrence time of the each trajectory data value plotted on the one trajectory graph in a superimposed manner on the one trajectory graph is generated.

11. The biological information analysis method according to claim 7, further comprising generating reference display data for displaying, together with the one trajectory graph, reference information including at least one of a transition direction of the one trajectory graph and predetermined feature amounts calculated from the one trajectory graph.

12. The biological information analysis method according to claim 7, wherein the first electrode is one of a transmission coil and a reception coil and the second electrode is another of the transmission coil and the reception coil, the transmission coil and the reception coil transmitting and receiving a high-frequency signal.

* * * * *